US012702790B2

(12) United States Patent
Murray et al.

(10) Patent No.: US 12,702,790 B2
(45) Date of Patent: Aug. 11, 2026

(54) REUSABLE URINARY CATHETER KITS

(71) Applicant: Hollister Incorporated, Libertyville, IL (US)

(72) Inventors: Michael G. Murray, Ballina (IE); Horacio Montes De Oca, Ballina (IE); Gary W. Inglese, Deerfield, IL (US); Rebecca M. Leece, Bicester (GB); Vincent Naughton, Sligo (IE); Daniel E. O'Brien, Calry (IE); David J. Farrell, Ballina (IE); David Hannon, Ballina (IE); Martin Bruggeman, Dublin (IE)

(73) Assignee: Hollister Incorporated, Libertyville, IL (US)

( * ) Notice: Subject to any disclaimer, the term of this patent is extended or adjusted under 35 U.S.C. 154(b) by 1286 days.

(21) Appl. No.: 17/616,620

(22) PCT Filed: Jun. 10, 2020

(86) PCT No.: PCT/US2020/037027
§ 371 (c)(1),
(2) Date: Dec. 3, 2021

(87) PCT Pub. No.: WO2020/252045
PCT Pub. Date: Dec. 17, 2020

(65) Prior Publication Data

US 2022/0226604 A1 Jul. 21, 2022

Related U.S. Application Data

(60) Provisional application No. 62/861,155, filed on Jun. 13, 2019.

(51) Int. Cl.
*A61M 25/00* (2006.01)
*A61L 2/08* (2026.01)
(Continued)

(52) U.S. Cl.
CPC ............ *A61M 25/002* (2013.01); *A61L 2/08* (2013.01); *A61L 2/18* (2013.01); *A61L 2103/15* (2026.01); *A61M 2025/0019* (2013.01)

(58) Field of Classification Search
CPC ......... A61M 25/002; A61M 2025/0019; A61L 2/08; A61L 2/18; A61L 2202/24;
(Continued)

(56) References Cited

U.S. PATENT DOCUMENTS 1,120,549 A 12/1914 Schellberg
3,794,042 A 2/1974 De Klotz et al.
(Continued)

FOREIGN PATENT DOCUMENTS

DE 3819257 C1 7/1989
DE 10334372 A1 2/2005
(Continued)

OTHER PUBLICATIONS

International Search Report and Written Opinion Dated Oct. 2, 2020 for International Application No. PCT/US2020/037027.

*Primary Examiner* — Michael J Tsai
*Assistant Examiner* — Justin L Zamory
(74) *Attorney, Agent, or Firm* — Cook Alex Ltd.

(57) ABSTRACT

Kits are provided for storing, transporting, and sterilizing reusable urinary catheters. A reusable urinary catheter stored within a housing of the kit may be sterilized between uses using a sterilization fluid or sterilizing light. If the reusable urinary catheter is sterilized using a sterilization fluid, the housing may include a manually actuated or electro-mechanical pump to circulate the sterilization fluid through the housing. The reusable urinary catheter may include a funnel secured to a catheter shaft, with a plurality of lateral openings defined in the funnel, which provide fluid communica-
(Continued)

tion between an interior of the funnel and an external surface of the catheter shaft. By allowing fluid communication between the interior of the funnel and the external surface of the catheter shaft, the lateral openings allow for fluid sterilization of both internal and external surfaces of the catheter shaft.

29 Claims, 14 Drawing Sheets

(51) Int. Cl.
*A61L 2/18* (2026.01)
*A61L 103/15* (2026.01)

(58) Field of Classification Search
CPC ......... A61B 1/121; A61B 1/123; A61B 1/126; A61B 90/70
See application file for complete search history.

(56) References Cited

U.S. PATENT DOCUMENTS 3,956,011 A 5/1976 Carleton
4,170,996 A 10/1979 Wu
4,346,706 A 8/1982 Leveen
4,754,877 A 7/1988 Johansson et al.
5,037,623 A * 8/1991 Schneider .......... B65D 81/3216 422/417
5,120,322 A 6/1992 Davis
5,207,705 A 5/1993 Trudell
5,226,530 A 7/1993 Golden
5,292,802 A 3/1994 Rhee
5,369,131 A 11/1994 Poli
5,451,406 A 9/1995 Lawin
5,718,862 A 2/1998 Thompson
5,768,853 A * 6/1998 Bushnell ................ B65B 9/042 53/167
5,800,412 A 9/1998 Zhang
6,113,629 A 9/2000 Ken
6,129,956 A 10/2000 Morra
6,352,710 B2 3/2002 Sawhney
6,361,751 B1 * 3/2002 Hight, III ................. A61L 2/18 422/294
6,387,080 B1 5/2002 Rødsten
6,409,723 B1 6/2002 Edwards
6,419,673 B1 7/2002 Edwards
6,524,608 B2 2/2003 Ottoboni
6,535,768 B1 3/2003 Baker
6,548,487 B2 4/2003 Takahashi
6,607,525 B2 8/2003 Franco
6,695,831 B1 2/2004 Tsukada et al.
7,014,861 B2 3/2006 Roorda
7,125,858 B2 10/2006 Filion
7,235,107 B2 6/2007 Evans
7,390,525 B2 6/2008 Epstein
7,537,589 B2 5/2009 Tsukada et al.
7,767,652 B2 8/2010 Hendriks
7,857,804 B2 12/2010 McCaffrey
7,862,552 B2 1/2011 McIntyre
7,918,819 B2 4/2011 Karmarkar
7,976,847 B2 7/2011 Southard
8,158,187 B2 4/2012 Chen
8,163,326 B2 4/2012 Zhong
8,235,937 B2 8/2012 Palasis
8,252,738 B2 8/2012 Marx
8,267,919 B2 9/2012 Utas
8,461,104 B2 6/2013 Bengmark
8,580,551 B2 11/2013 Kaplan
8,585,753 B2 11/2013 Scanlon
8,617,542 B2 12/2013 Madhyastha
8,646,445 B2 2/2014 Fine
8,680,228 B2 3/2014 Guo
8,685,427 B2 4/2014 Li
8,703,180 B1 4/2014 Stankus
8,709,465 B2 4/2014 Chen
8,889,211 B2 11/2014 Owens
8,911,424 B2 12/2014 Weadock
8,916,227 B2 12/2014 Horres
8,933,416 B2 1/2015 Arcand et al.
9,132,151 B2 9/2015 Ko
9,226,926 B2 1/2016 Ueda
9,295,663 B2 3/2016 Pacetti
9,364,513 B2 6/2016 Ellis-Behnke
9,415,084 B2 8/2016 Ellis-Behnke
9,724,448 B2 8/2017 Kobayashi
9,884,028 B2 2/2018 Holzer
10,076,537 B2 9/2018 Marcum
10,137,287 B2 11/2018 Sansone
10,172,978 B2 1/2019 Wedlin
10,227,718 B2 3/2019 Cahil
10,232,143 B2 3/2019 Rajagopalan
10,525,172 B2 1/2020 Martin
10,532,132 B2 1/2020 Tobias
10,537,375 B2 1/2020 Wang
10,583,237 B2 3/2020 Feld
10,639,400 B2 5/2020 Sartor
10,695,461 B2 6/2020 Suppiger
10,791,735 B2 10/2020 Thomas
10,806,830 B2 10/2020 Wang
10,829,520 B2 11/2020 Obrecht
10,849,324 B2 12/2020 Sawyer
10,987,208 B2 4/2021 Schaefer
11,001,612 B2 5/2021 Zlotkin
11,001,688 B2 5/2021 Niu
11,098,203 B2 8/2021 Ozcelik
11,541,205 B2 1/2023 Erbey, II
2002/0058631 A1 5/2002 Cai
2003/0017073 A1 1/2003 Eckhardt et al.
2003/0130228 A1 7/2003 Chen
2003/0181388 A1 9/2003 Cai
2003/0191064 A1 10/2003 Kopke
2004/0005423 A1 1/2004 Dalton
2004/0047892 A1 3/2004 DesRosiers
2004/0049134 A1 3/2004 Tosaya
2004/0092821 A1 5/2004 Hering
2004/0151702 A1 8/2004 Marksteiner
2004/0197784 A1 10/2004 Miano
2004/0215231 A1 10/2004 Fortune
2005/0003010 A1 1/2005 Cohen
2005/0013812 A1 1/2005 Dow
2005/0033374 A1 2/2005 Gerber
2005/0163818 A1 7/2005 Sung
2006/0025753 A1 2/2006 Kubalak et al.
2006/0093644 A1 5/2006 Quelle
2006/0134186 A1 6/2006 Carlton
2007/0066963 A1 3/2007 Tanghoj
2007/0239107 A1 10/2007 Lundberg
2008/0091145 A1 4/2008 House
2008/0103481 A1 5/2008 Vogel
2008/0177217 A1 7/2008 Polaschegg
2008/0200907 A1 8/2008 Nestenborg
2008/0200924 A1 8/2008 Burbank
2008/0242614 A1 10/2008 Fraser
2008/0275015 A1 11/2008 Potter
2008/0311172 A1 12/2008 Schapira
2009/0071851 A1 3/2009 Maki et al.
2009/0098187 A1 4/2009 Peters
2009/0101531 A1 4/2009 Nordholm et al.
2009/0171317 A1 7/2009 Versi
2009/0227981 A1 9/2009 Bennett
2009/0299334 A1 12/2009 Nishtala et al.
2010/0198195 A1 8/2010 Nishtala
2010/0331819 A1 12/2010 Hossainy
2011/0091515 A1 4/2011 Zilberman
2011/0114520 A1 5/2011 Matthison-Hansen
2011/0137296 A1 6/2011 Tanghoj
2011/0142901 A1 6/2011 Brandon
2012/0168324 A1 7/2012 Carleo
2012/0179145 A1 7/2012 Nishtala
2012/0245518 A1 9/2012 Lovasz
2012/0316515 A1 12/2012 Terry
2013/0267888 A1 10/2013 Rhodes et al.
2014/0236082 A1 8/2014 Roorda

(56) References Cited

U.S. PATENT DOCUMENTS

| | | | |
|---|---|---|---|
| 2014/0264074 | A1 | 9/2014 | Victor et al. |
| 2015/0367029 | A1 | 12/2015 | DeVore |
| 2016/0331841 | A1 | 11/2016 | Prestwich |
| 2017/0065519 | A1 | 3/2017 | Zilberman |
| 2017/0106120 | A1 | 4/2017 | McClendon |
| 2017/0136127 | A1 | 5/2017 | Maki |
| 2017/0165194 | A1 | 6/2017 | Meng |
| 2018/0169377 | A1 | 6/2018 | Hickmott et al. |
| 2018/0207323 | A1 | 7/2018 | Chen |
| 2018/0236141 | A1 | 8/2018 | Russell |
| 2018/0338475 | A1 | 11/2018 | Ala'Aldeen et al. |
| 2019/0030184 | A1 | 1/2019 | Kidambi |
| 2019/0046488 | A1 | 2/2019 | Rosenblatt |
| 2019/0175104 | A1 | 6/2019 | Malik |
| 2019/0262500 | A1 | 8/2019 | Xu |
| 2019/0269816 | A1 | 9/2019 | Williams |
| 2019/0375149 | A1 | 12/2019 | Limem |
| 2020/0009214 | A1 | 1/2020 | Gil |
| 2020/0056063 | A1 | 2/2020 | Wilson |
| 2020/0190511 | A1 | 6/2020 | Olson |
| 2020/0197562 | A1 | 6/2020 | Xue |
| 2020/0368159 | A1 | 11/2020 | Chen |
| 2020/0392465 | A1 | 12/2020 | Sanghavi |
| 2021/0015993 | A1 | 1/2021 | O'Neill |
| 2021/0145749 | A1 | 5/2021 | Tagil |
| 2022/0016398 | A1 | 1/2022 | Li |
| 2022/0233437 | A1 | 7/2022 | Borody |
| 2022/0257843 | A1 | 8/2022 | Testani |
| 2022/0273587 | A1 | 9/2022 | Parsons |
| 2022/0273698 | A1 | 9/2022 | Lovasz |
| 2022/0280682 | A1 | 9/2022 | Bodkhe |
| 2022/0370688 | A1 | 11/2022 | Sileika |

FOREIGN PATENT DOCUMENTS

| | | | |
|---|---|---|---|
| DE | 102004013712 | B3 | 8/2005 |
| EP | 0751796 | A1 | 1/1997 |
| EP | 0887373 | A2 | 12/1998 |
| EP | 1087795 | A1 | 4/2001 |
| EP | 1181023 | B1 | 2/2002 |
| EP | 1060204 | B1 | 6/2002 |
| EP | 1214039 | A2 | 6/2002 |
| EP | 1070502 | B1 | 6/2003 |
| EP | 1324785 | B1 | 4/2004 |
| EP | 1589888 | A2 | 11/2005 |
| EP | 1272227 | B1 | 4/2006 |
| EP | 1264613 | B1 | 2/2007 |
| EP | 1682124 | B1 | 12/2007 |
| EP | 1476204 | B1 | 10/2008 |
| EP | 1433485 | B1 | 11/2009 |
| EP | 2259788 | A2 | 12/2010 |
| EP | 2379059 | A1 | 10/2011 |
| EP | 2402043 | A1 | 1/2012 |
| EP | 2411440 | B1 | 2/2012 |
| EP | 2788040 | B1 | 10/2014 |
| EP | 2231254 | B9 | 4/2015 |
| EP | 2860194 | B1 | 4/2015 |
| EP | 2911735 | B1 | 9/2015 |
| EP | 2793962 | B1 | 4/2016 |
| EP | 1912627 | B1 | 8/2016 |
| EP | 3065807 | A1 | 9/2016 |
| EP | 3119447 | A1 | 1/2017 |
| EP | 3148334 | A1 | 4/2017 |
| EP | 3234000 | A1 | 10/2017 |
| EP | 3242657 | A1 | 11/2017 |
| EP | 2437844 | B1 | 5/2018 |
| EP | 2919846 | B1 | 4/2019 |
| EP | 3419597 | B1 | 12/2019 |
| EP | 2776079 | B1 | 4/2020 |
| EP | 3057617 | B1 | 4/2020 |
| EP | 3706816 | A1 | 9/2020 |
| EP | 3052111 | B1 | 12/2020 |
| EP | 3746112 | A1 | 12/2020 |
| EP | 3750523 | A1 | 12/2020 |
| EP | 3750524 | A1 | 12/2020 |
| EP | 3791865 | A1 | 3/2021 |
| EP | 3810085 | A1 | 4/2021 |
| EP | 3810094 | A1 | 4/2021 |
| EP | 3810095 | A1 | 4/2021 |
| EP | 3810268 | A1 | 4/2021 |
| EP | 3917584 | A1 | 12/2021 |
| EP | 3924031 | A1 | 12/2021 |
| EP | 3937994 | A1 | 1/2022 |
| EP | 3941542 | B1 | 1/2022 |
| EP | 3974007 | A1 | 3/2022 |
| EP | 4031131 | A1 | 7/2022 |
| EP | 4045054 | A1 | 8/2022 |
| EP | 4048229 | A1 | 8/2022 |
| EP | 4048298 | A1 | 8/2022 |
| EP | 4087558 | A1 | 11/2022 |
| JP | 2011139881 | A | 7/2011 |
| JP | 2011139882 | A | 7/2011 |
| WO | 1989003232 | A1 | 4/1989 |
| WO | 2002020005 | A1 | 3/2002 |
| WO | 2002024248 | A1 | 3/2002 |
| WO | 2004030706 | A2 | 4/2004 |
| WO | 2004066875 | A1 | 8/2004 |
| WO | 2005018600 | A2 | 3/2005 |
| WO | 2005058200 | A1 | 6/2005 |
| WO | 2005092418 | A1 | 10/2005 |
| WO | 2005092419 | A1 | 10/2005 |
| WO | 2006002365 | A2 | 1/2006 |
| WO | 2012034032 | A2 | 3/2012 |
| WO | 2013049033 | A1 | 4/2013 |
| WO | 2014139809 | A1 | 9/2014 |
| WO | 2015074730 | A1 | 5/2015 |
| WO | 2015075841 | A1 | 5/2015 |
| WO | 2015089189 | A2 | 6/2015 |
| WO | 2015184365 | A1 | 12/2015 |
| WO | 2016159859 | A1 | 10/2016 |
| WO | 2016206701 | A1 | 12/2016 |
| WO | 2018053111 | A1 | 3/2018 |
| WO | 2018153514 | A1 | 8/2018 |
| WO | 2019104213 | A1 | 5/2019 |
| WO | 2021089470 | A1 | 5/2021 |
| WO | 2021168284 | A1 | 8/2021 |
| WO | 2022055559 | A1 | 3/2022 |

* cited by examiner 46
44
10
18
14
16
20

44
10
18
26
28
16
14
20

REUSABLE URINARY CATHETER KITS

CROSS-REFERENCE TO RELATED APPLICATION

This application is a National Stage Entry of International Application No. PCT/US2020/037027, filed Jun. 10, 2020, which claims the benefit of U.S. Provisional Application Ser. No. 62/861,155, filed Jun. 13, 2019, all of which are hereby incorporated by reference in their entirety.

BACKGROUND

Field of the Disclosure

The present disclosure generally relates to urinary catheters. More particularly, the present disclosure relates to reusable urinary catheter kits.

Description of Related Art

Catheters are used to treat many different types of medical conditions and typically include an elongated shaft that is inserted into and through a passageway or lumen of the body. Catheters, and in particular intermittent catheters, are commonly used by those who suffer from various abnormalities of the urinary system, such as urinary retention or incontinence. With the advent of intermittent catheters, individuals with urinary system abnormalities can self-insert and self-remove intermittent catheters several times a day.

Urinary catheters are frequently provided as disposable, single-use items. A user will remove the catheter from a package, use the catheter once, and then dispose of the catheter and the package. Reusable urinary catheters could, thus, be advantageous in reducing the amount of waste created by the use disposable catheters, but there are various challenges associated with the use of reusable catheters (including storage, transport, and sterilization) that must be overcome before widespread acceptance and use of reusable catheters.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a reusable urinary catheter kit including a housing having a base defining a disinfecting chamber. The base having a bottom end and a top end wherein the top end of the base defines an opening of the disinfecting chamber. The housing also including a lid associated with the top end of the base. The lid being movable between a closed condition and an open condition. In the closed condition, the lid overlaying the base and covering the opening of the disinfecting chamber and in the open condition the lid is moved away from the base to uncover the opening of the disinfecting chamber. The kit also including a chassis removably positioned within the housing and a reusable urinary catheter removably secured to the chassis. The kit also including a removable supply of sterilization fluid in fluid communication with the disinfecting chamber and a waste tank in communication with the disinfecting chamber.

In another aspect, a method for sterilizing a reusable urinary catheter that includes securing a reusable urinary catheter to a chassis. The chassis is then positioned into a housing including a base and a lid. The lid is moved from an open condition to a closed condition overlaying the base. The reusable catheter is then sterilized within the housing.

DESCRIPTION OF THE ILLUSTRATED EMBODIMENTS

Figures 1, 2:
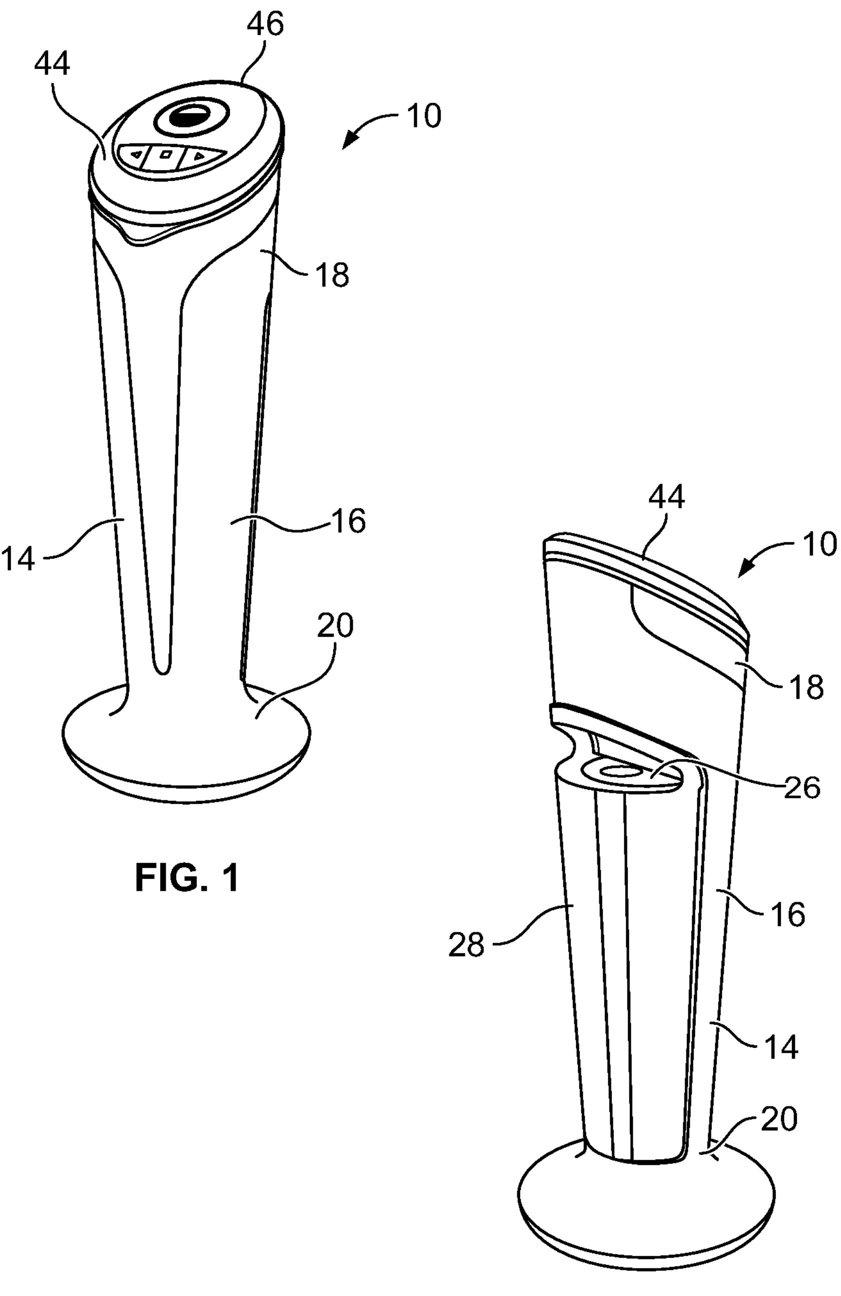
FIG. 1 is a front perspective view of one embodiment of a reusable urinary catheter kit according to an aspect of the present disclosure, with a housing of the kit in a closed condition.
FIG. 2 is a rear perspective view of the reusable urinary catheter kit of FIG. 1.
Figure 3:
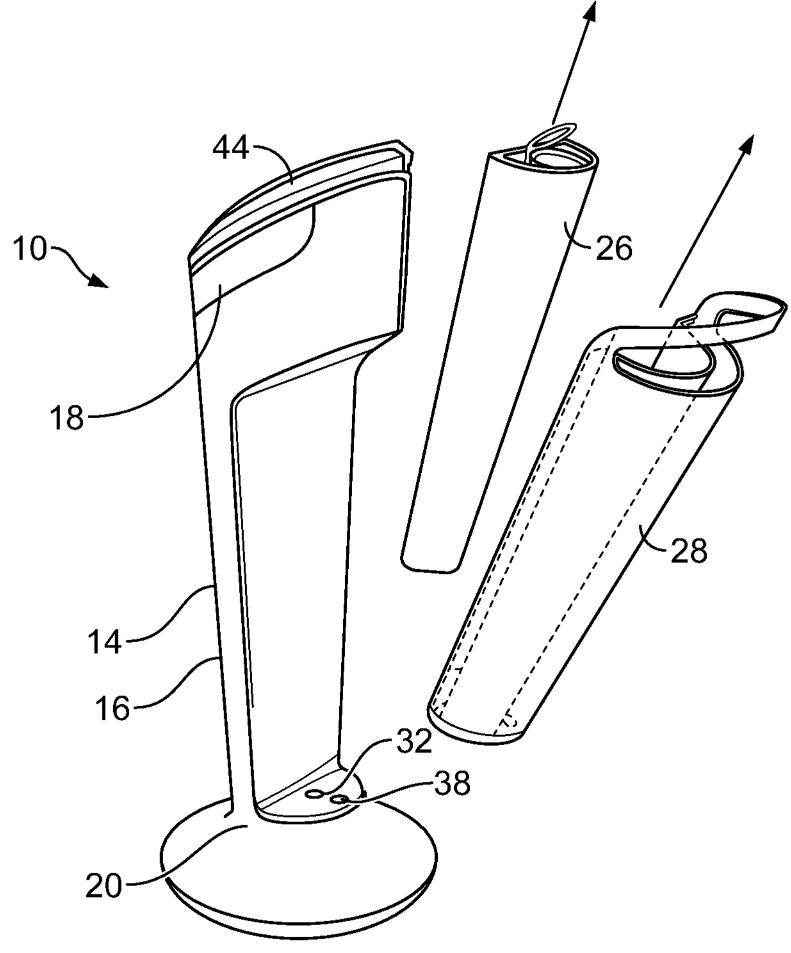
FIG. 3 is a rear perspective view of the reusable urinary catheter kit of FIG. 1, shown with the sterilization supply and waste tank removed from the housing.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Reusable urinary catheter kits according to the present disclosure and their individual components may be variously configured without departing from the scope of the present disclosure, but in one embodiment, a reusable urinary catheter kit 10 is configured as shown in FIG. 1-4. FIGS. 5-13 illustrate a method of using and then sterilizing a reusable urinary catheter 12 (FIGS. 6-8) of the kit 10. In the embodiment of FIGS. 1-5, 9 and 11-13, the kit 10 includes a housing or body 14 having a base 16 with top and bottom ends 18 and 20. The outer shape of the kit is generally cylindrical or conical in shape. The base 16 defines a disinfecting chamber 22 (FIGS. 4, 5 and 9) that has an opening 24 defined by the top end 18 of the base 16.

The kit 10 also includes a supply of the sterilization fluid, such as the illustrated cartridge or tank 26, and a waste collection tank 28, which are both removably attachable to the housing 14 (FIGS. 2, 4, 12 and 13). One or both of the cartridge 26 and waste tank 28 may be disposable. The sterilization fluid may be any suitable biocompatible sterilization fluid. Such fluids may include antimicrobial agents, such as agents that kill bacteria, viruses or other microbes, agents that prevent microbial growth, anti-adherence agents that prevent microbes from adhering to the surfaces, etc. Furthermore, when the catheter 12 includes a hydrophilic catheter tube that has an outer hydrophilic surface that becomes lubricous when wetted or hydrated, the sterilization fluid may also serve as a hydration fluid that hydrates the hydrophilic surface. The lubricious hydrophilic outer surface assists in inserting the catheter into and retracting the catheter out of the urethra. In other embodiments, the sterilization fluid may include a lubricant, such as oil or water based lubricants that lubricates the outer surface. In yet other embodiments, the user may apply a lubricant just prior to use.

The sterilization fluids also may be a fluid that can be formed into a foam. Such fluids may include a surface tension reducing agent and a foam stabilization agent. The surface tension reducing agent may assist in adding or incorporating gas bubbles into the sterilization fluid to form a foam. In one embodiment, the surface tension reducing agent may be a surfactant or a mixture of surfactants. The surface tension reducing agent may be a foaming agent. The foam stabilizer may slow coalescence of the foam. In one embodiment, the sterilization fluid may include an antimicrobial agent and a surfactant (e.g., sodium dodecyl sulphate or sodium methyl cocoyl taurate) and a stabilizer (e.g., Xanthan gum). The sterilization fluid can be transformed into a foam by homogenizing air with the fluid. The air may be homogenized with the sterilization fluid by agitation of the fluid in the presence of air. The agitation can be a result of an agitation mechanism, such as a pump, restriction, homogenizer, etc.

Turning back to FIGS. 2, 4, 12 and 13, the cartridge 26 and waste tank 28 also may have complementary shapes that allow the cartridge 26 and waste tank 28 to engage, nest, dovetail or otherwise fit together. For example, in the illustrated embodiment, the waste tank 28 has a generally outer u-shaped configuration wherein the cartridge 26 has a generally outer curved configuration that is commensurate with the inner curvature of the u-shape of the waste tank 28. This allows the cartridge 26 to nest with the waste tank 28. In one embodiment, there is a friction fit between the cartridge 26 and waste tank 28, such that the two are removably attached to each other. In another embodiment, the two may also be attached with a peg in slot attachment. The shapes of the cartridge 26 and the waste tank 28 could be switched and the waste tank 28 could nest within the cartridge 26. In yet another embodiment, the waste tank 28 and cartridge 26 may not be in any physical contact.

Figure 4:
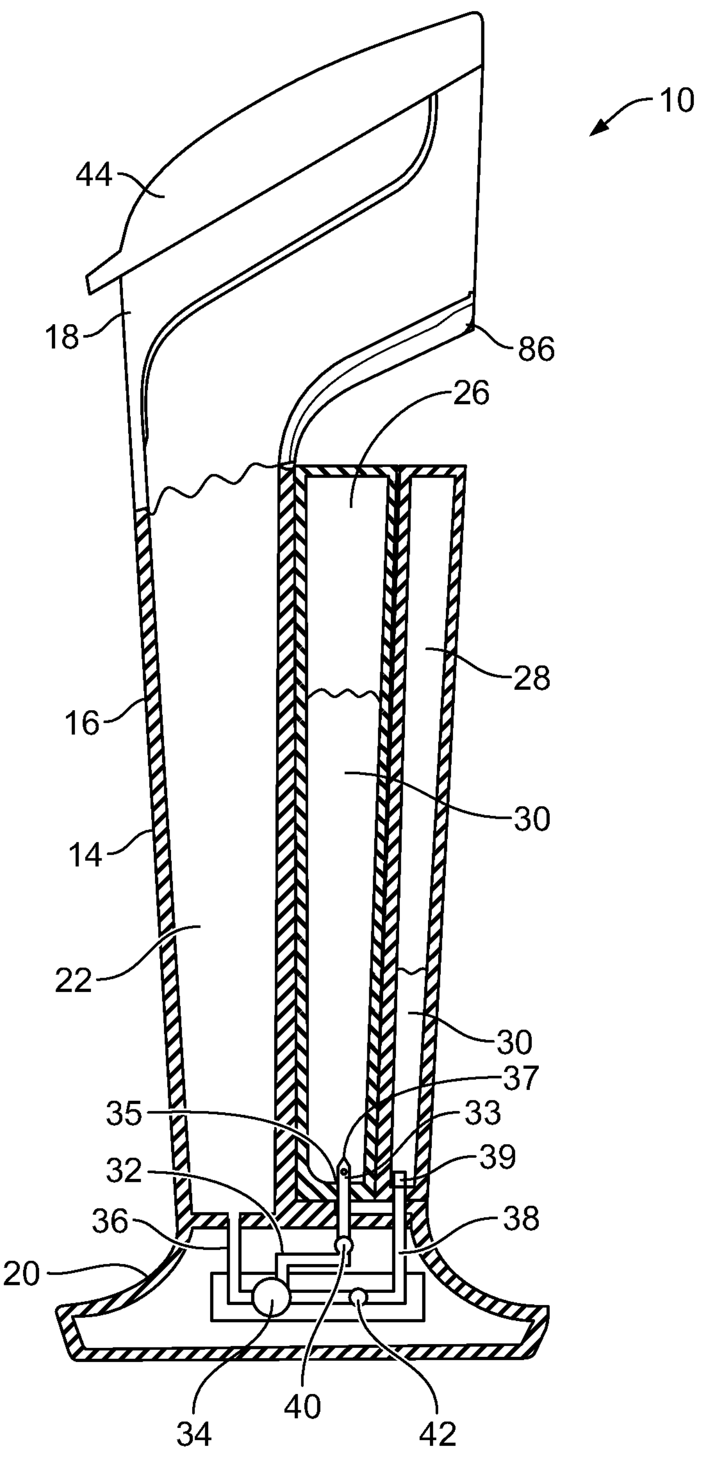
FIG. 4 is a partial cross-sectional view of the reusable urinary catheter kit of FIG. 1.

When attached to the housing 14, the cartridge 26 and the waste tank 28 may be in selective fluid communication with the disinfecting chamber 22. Referring to FIG. 4, sterilization fluid 30 may flow from the cartridge 26 through a supply flow path 32 to a pump 34. As illustrated in FIG. 4, optionally, the base 16 may include an upright 33 that extends into bottom opening 35 of the cartridge 26. The upright 33 may include one or more eyelets or opening 37 to allow fluid flow. The pump 34 may pump a select amount of sterilization fluid 30 through fill/drain flow path 36 into the disinfecting chamber 22. After disinfecting, the sterilization fluid 30 may flow through fill/drain flow path 36 back to pump 34, which may be a revisable pump. Pump 34 pumps the sterilization fluid 30 through waste flow path 38 to waste tank 28. The waste tank 28 may include a reclosable valve 39, such as a lift check valve, that allows spent fluid into the waste tank 28, but does not allow fluid out of the tank. Also, the supply flow path 32 and the waste flow path 38 may include valves 40 and 42 that are actuated during the filling and draining of the sterilization chamber 22. For example, when sterilization fluid 30 is being pumped from the cartridge 26 to the sterilization chamber 22, valve 40 may be open and valve 42 may be closed. When sterilization fluid 30 is being drained from the sterilization chamber 22, valve 42 may be open and valve 40 may be closed.

A lid 44 is associated with the top end 18 of the base 16. The lid 44 is movable between a closed condition, in which the lid covers the opening 24 of the disinfecting chamber 22 (as in FIG. 1) and an open condition in which the lid 44 does not cover opening 24 (as in FIG. 5). In the illustrated embodiment, the lid 44 is pivotally secured to the top end 18 of the base 16. The lid 44 is movable between the closed condition, in which the lid 44 is pivoted toward the base 16 (as in FIG. 1) and an open condition in which the lid 44 is pivoted away from the base 16 (as in FIG. 5). More particularly, in the closed condition, the lid 44 is positioned to contact and overlay the base 16, covering the disinfecting chamber opening 24. The base 16 and lid 44 may be formed of a generally rigid material, such as a plastic material. The lid may also include the user interface 46, which the user interacts with to commence sterilization and which provides the user with an indication of stages of the sterilization process.

Figure 5:
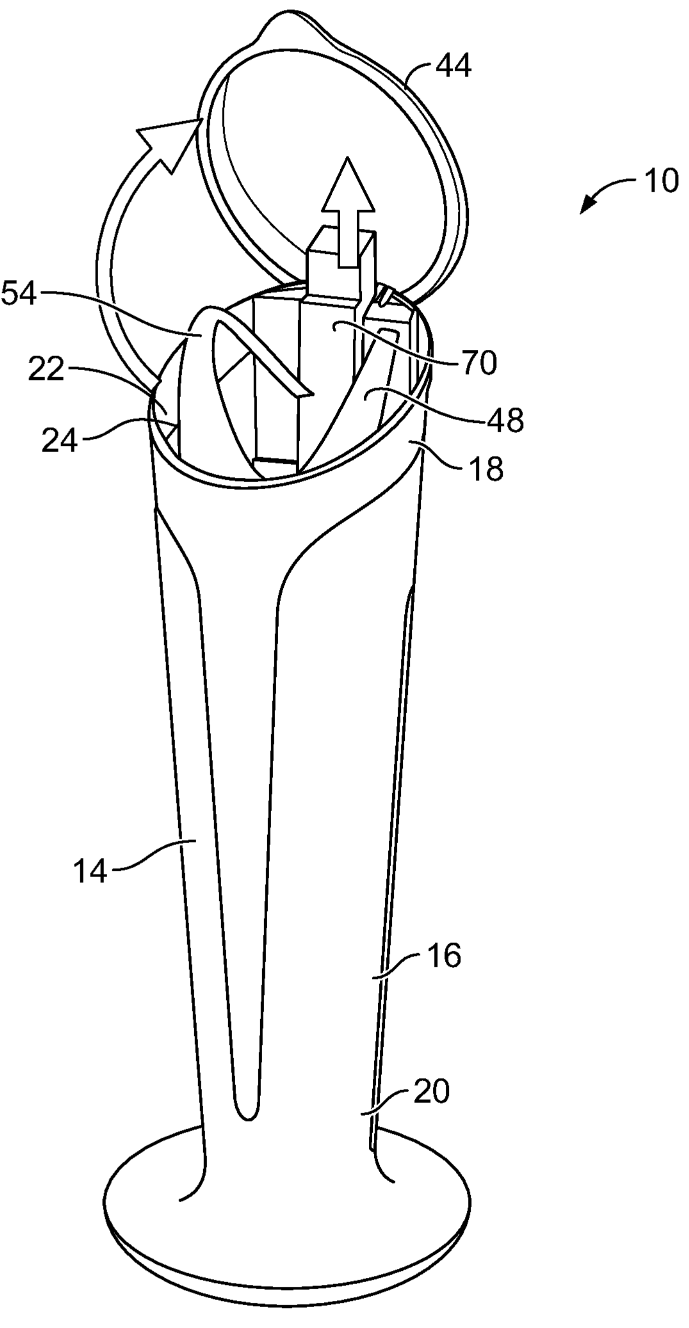
FIG. 5 is a front perspective view of the reusable urinary catheter kit of FIG. 1, with the housing of the kit in an open configuration.
Figure 9:
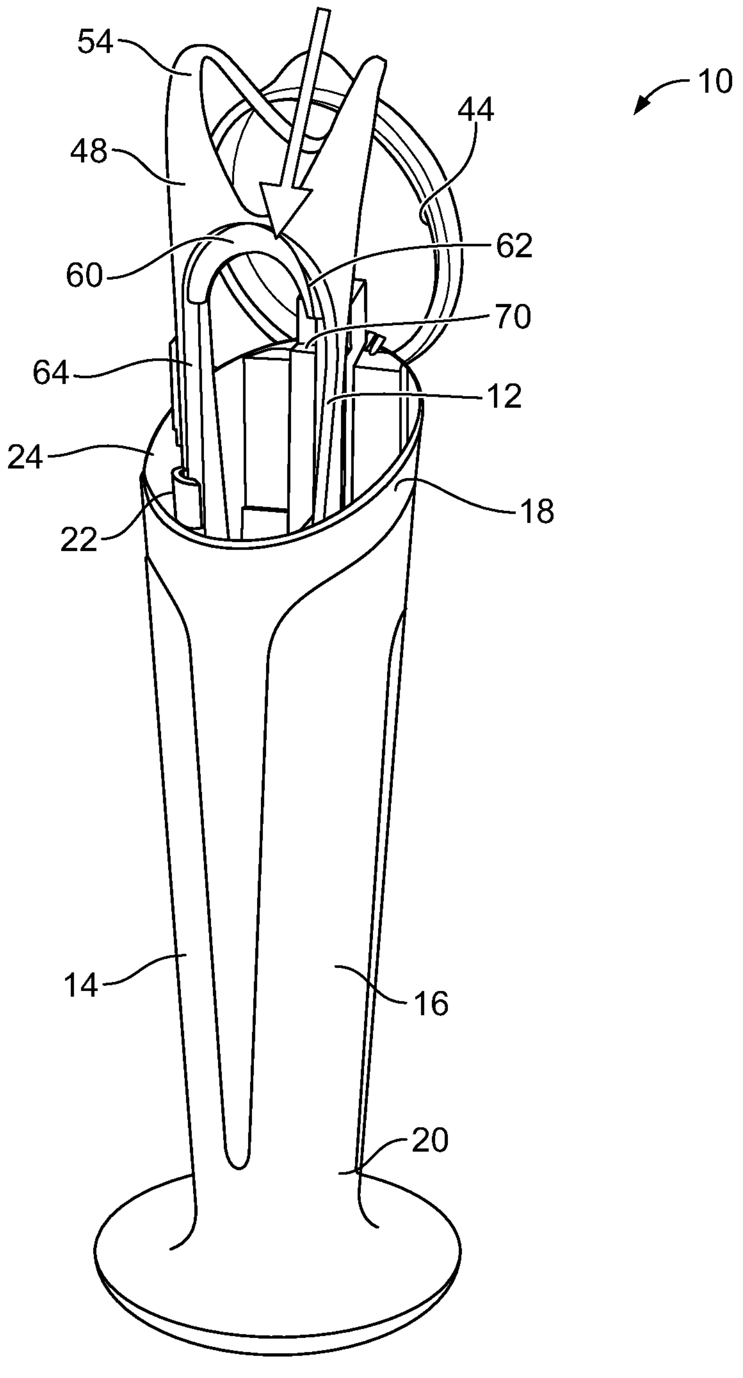
FIG. 9 is a perspective view of the reusable urinary catheter kit FIG. 1, with the chassis being placed into the housing.

Referring to FIGS. 5-9, chassis 48 is removably positioned within the disinfecting chamber 22 (FIGS. 5 and 9). The chassis 48 may be formed of a generally rigid material, such as a plastic material, with a reusable urinary catheter 12 removably secured to the chassis 48, such as by being at least partially wrapped around the chassis 48. The chassis 48 includes a body 50 having a frame 52 for holding the catheter 12 and a hook 54 extending from the frame 52 for handling and hanging the chassis 48.

The chassis 48 may be variously configured without departing from the scope of the present disclosure. In the illustrated embodiment, the frame 52 of the chassis 48 includes opposed catheter clips 56 and 58, with catheter tube 60 of the reusable urinary catheter 12 removably received by clips 56 and 58. The illustrated chassis 48 further includes at least one wall 60 between the clips 56 and 58. The wall 60 may be arcuate and it has a groove 62 that receives the catheter tube 64 to maintain the tube in a bent configuration.

Figure 6:
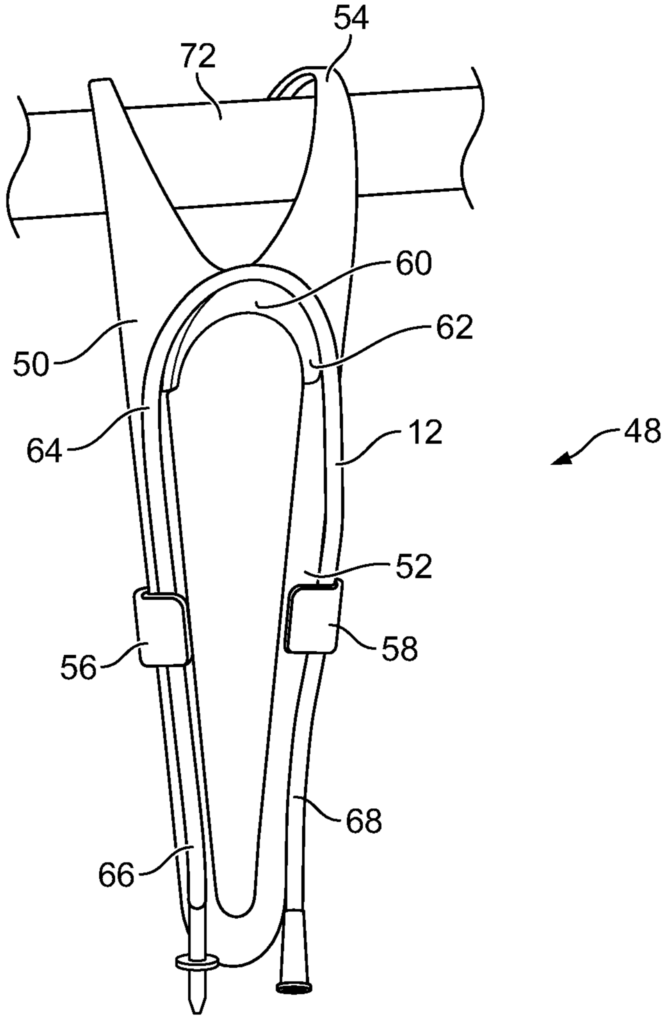
FIGS. 6-8 are perspective views of a chassis and reusable urinary catheter of the kit of FIG. 1.
Figures 7, 8:
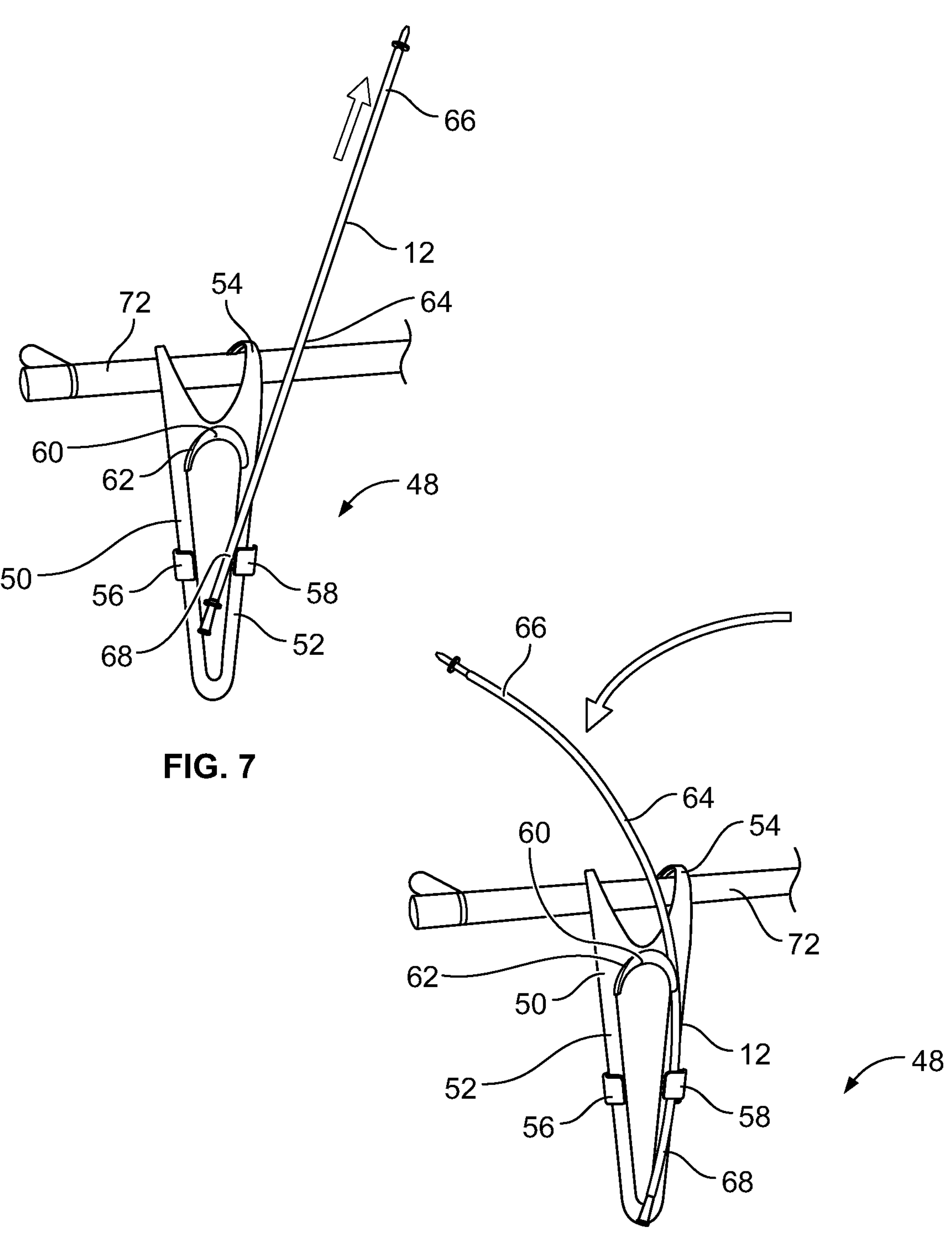

To secure the reusable urinary catheter 12 to the illustrated chassis 48, one of the proximal end 66 and the distal end 68 of the catheter tube 64 is pressed into one of the clips 56 and 58, followed by wrapping the catheter tube 64 around wall 60 of the frame, with a middle portion of the catheter tube received by the groove 62 of the wall (FIG. 8). The other end of the proximal and distal ends 66 and 68 of the catheter tube 64 is pressed into the other one of the clips 56 and 58 (FIG. 6). The installation process may be reversed to dissociate the reusable urinary catheter 12 from the chassis 48 (FIG. 7).

In use, the lid 44 of the housing 14 is opened and the user removes the chassis 48 from the disinfecting chamber 22. In the illustrated embodiment, the housing 14 includes a lifting mechanism 70 (FIGS. 5 and 9) that lifts the chassis 48 upward to allow easier access to the chassis for the user. The lifting mechanism 70 may include an arm that is connected to the lid 44, such that the arm moves upward when the lid is opened. The chassis 48 may be attached to the arm by engaging the hook portion 54 of the chassis 48 with a receiving groove on the arm, such that the chassis 48 hangs from the arm.

Next, the chassis 48 is removed from the base 16 (FIG. 5) and the reusable urinary catheter 12 is all or partially dissociated from the chassis 48 (FIG. 7), as described above. During dissociation of the catheter 12 from the chassis 48, the user may use the hook 52 to hang the chassis 48 on for example a towel bar 72 (FIGS. 6-8). The user then uses the reusable urinary catheter 12 for catheterization. Following catheterization, the reusable urinary catheter 12 is reconnected to the chassis 48 (FIG. 8) and then the chassis 48 is returned to the disinfecting chamber 22, as in FIG. 9. The lid 44 is then moved from its open condition to its closed condition, as in FIG. 1. The user then initiates the sterilization process in which the sterilization fluid flows from the cartridge 26 into the disinfecting chamber 22. The sterilization fluid remains within the disinfecting chamber 22 for a period time sufficient to sterilize the catheter. Optionally, an agitator or fluid circulator may be included in the disinfecting chamber 22 to move the sterilization fluid within the chamber. If the sterilization fluid comprises a foam, the agitator or fluid circulator may foam the sterilization fluid and/or the sterilization fluid may be foamed by the pump or a restriction in the supply line.

The sterilization fluid then is drained from the disinfecting chamber 22 and flows into the waste tank 28. After the sterilization fluid has been drained from the chamber 22 to the waste tank, the sterilization process in completed and the catheter 12 is ready to be reused for catheterization.

Optionally, at least one light source is associated with the base 16 and/or the lid 44 and is configured to irradiate at least a portion of the reusable urinary catheter 12 with light to refresh the hydrophilic coating, if one is present.

Figure 10A:
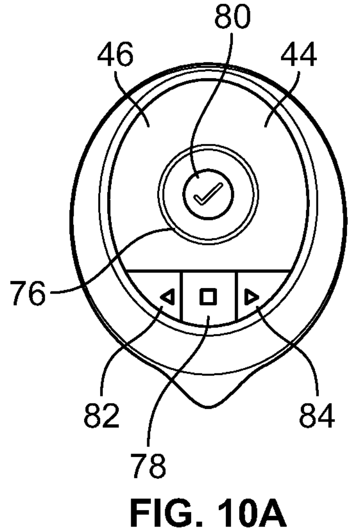
FIGS. 10*a*-10*d* illustrate the controls and user interface of the housing.
Figure 10B:
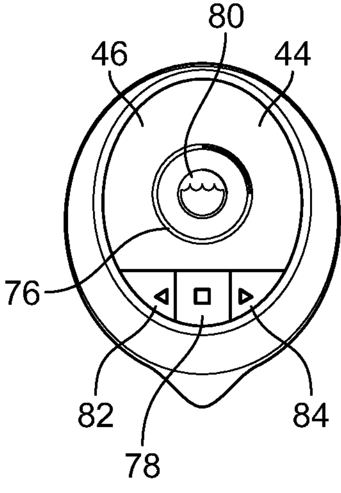
Figure 10C:
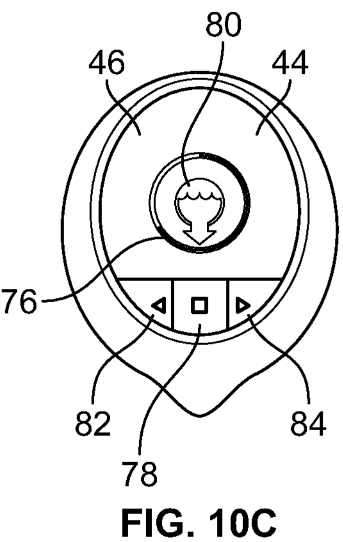
Figure 10D:
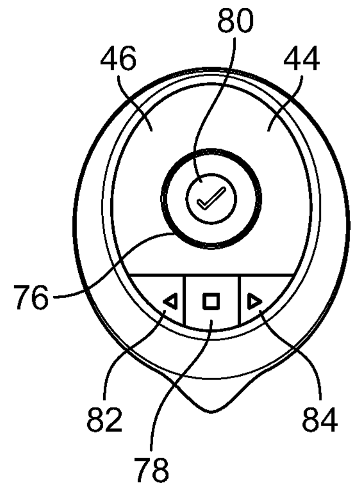
Figures 11, 12, 13:
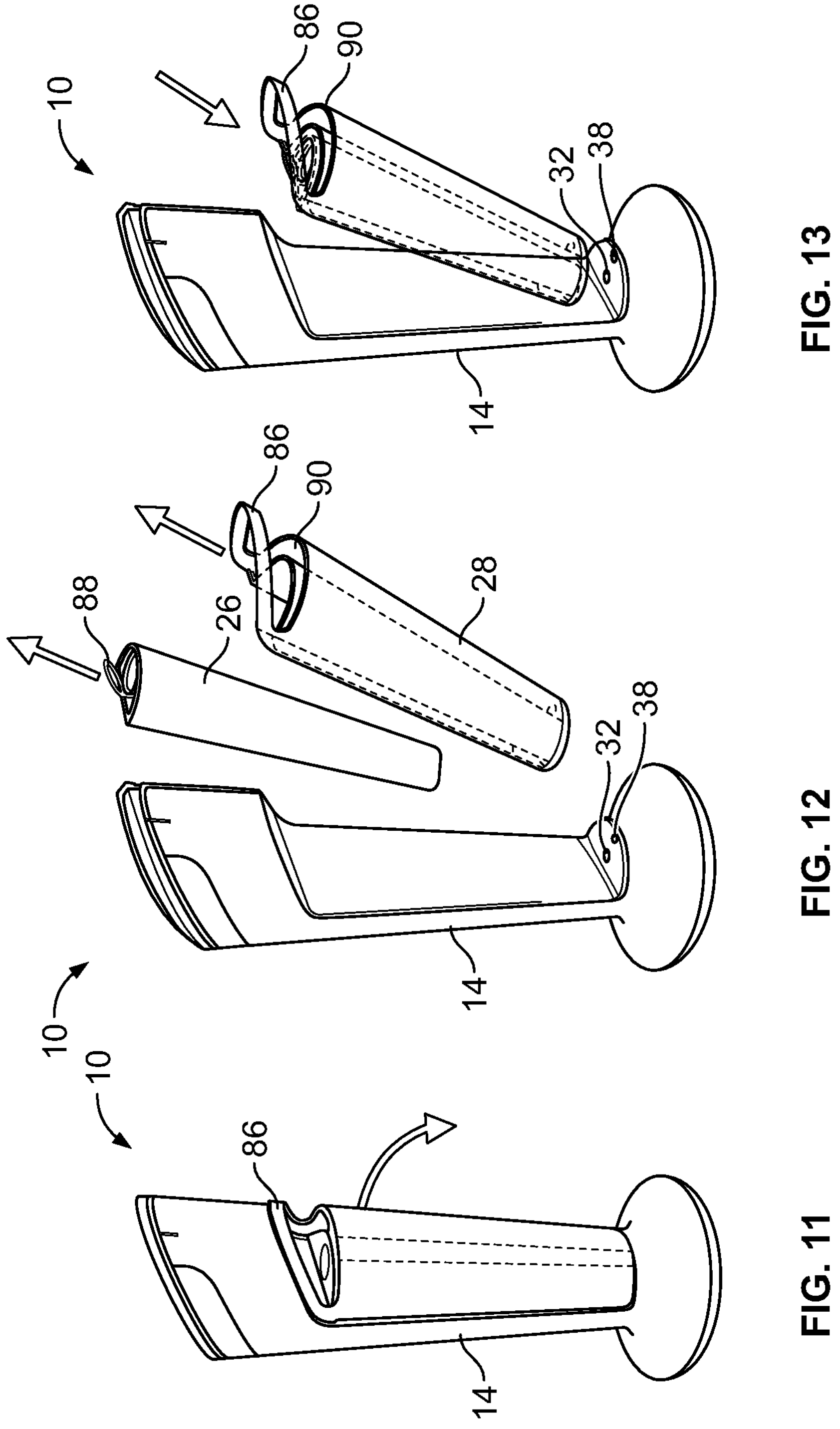
FIGS. 11-13 are perspective views of the reusable urinary catheter kit of FIG. 1, showing the removal and replacement of the sterilization fluid supply and the waste collection tank.
Figure 14:
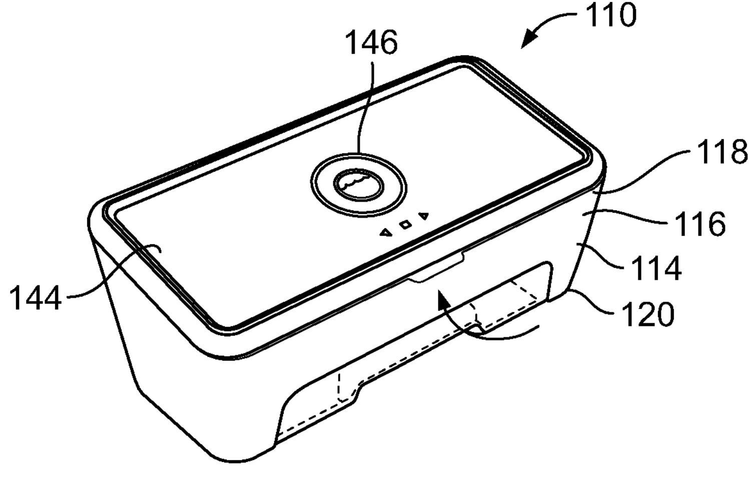
FIG. 14 is a front perspective view of another embodiment of a reusable urinary catheter kit according to an aspect of the present disclosure, with a housing of the kit in a closed condition.
Figure 15:
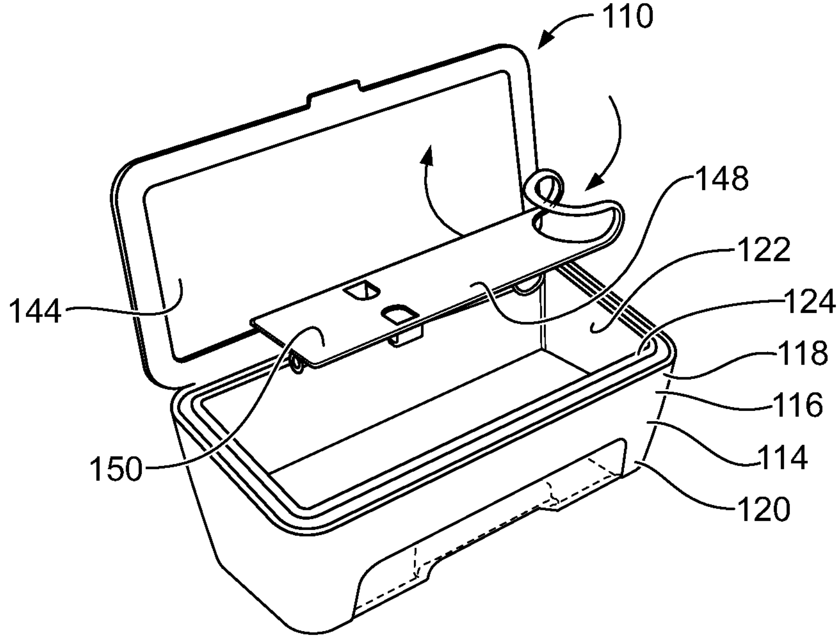
FIG. 15 is a front perspective view of the reusable urinary catheter kit of FIG. 14, with the housing of the kit in an open condition.
Figure 16:
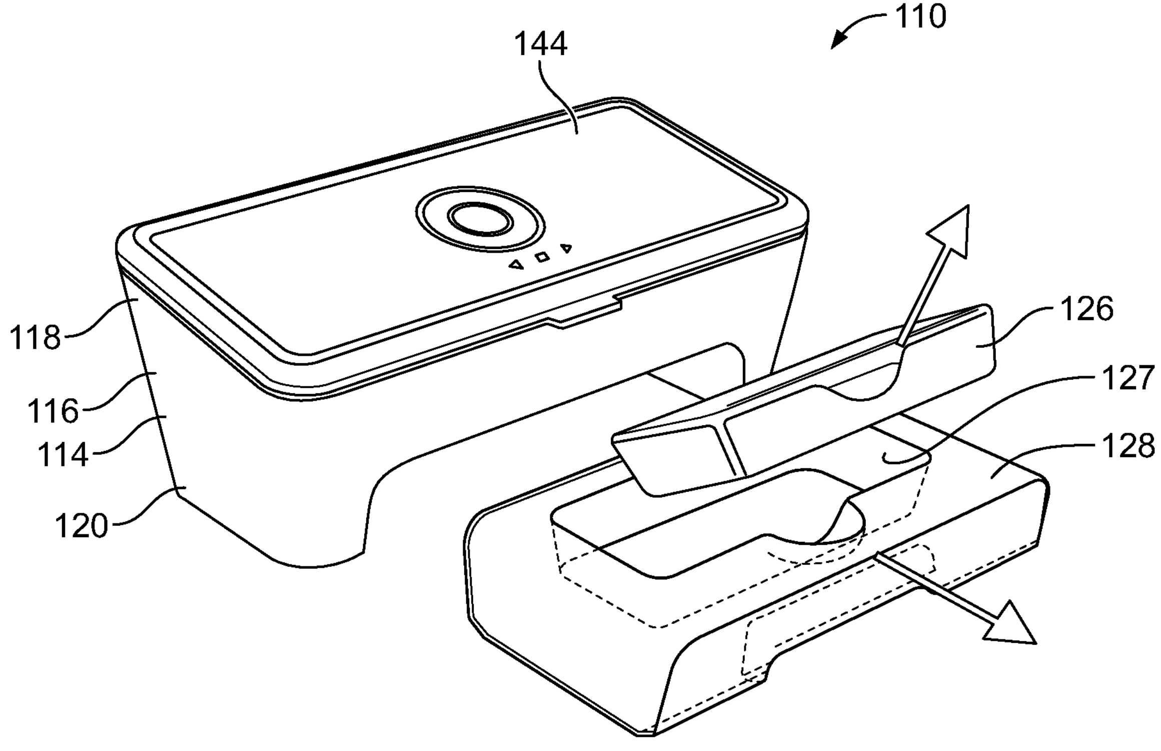
FIG. 16 is a perspective view of the reusable urinary catheter kit of FIG. 14, shown with the sterilization supply and waste tank removed from the housing.

FIGS. 10*a*-10*d* provide an exemplary user interface of the kit 10. After the chassis 48 and catheter 12 have been placed in the disinfecting chamber 22 and the lid 44 has been closed, the user interacts with the interface to commence sterilization. Referring to FIG. 10*a*, the interface may include a visual indicator indicating that the kit 10 is ready for use. In the illustrated embodiment, the ring 76 may be completely one color, indicting the kit is ready for use. The user may press a start button, such as the button 78, to commence sterilization. Referring to FIGS. 10*b* and 10*c*, as the sterilization process progresses, the ring 76 may gradually change colors to indicate the progress of the sterilization process. Optionally, an icon 80 may change appearance to indicate filling and draining of the disinfecting chamber 22. Referring to FIG. 10*d*, the ring 76 may change completely to the different color to indicate the completion of sterilization, and if an icon 80 is present, the icon also may indicate the completion. In the illustrated embodiment, the icon 80 includes a checkmark. The interface may also include buttons 82, 84 which allows the user to cycle through the different stages of sterilization, as needed.

Referring to FIGS. 3 and 11-13, after the cartridge 26 is spent or otherwise needs to be changed, the cartridge 26 and waste tank 28 may be detached from the housing 14. In the illustrated embodiment, the waste tank 28 includes a handle 86, which is grasped and pulled by the user to detach the waste tank 28 and cartridge from the housing 14. Referring to FIG. 4, the waste tank 28 may include a self-closing valve 39, such as a lift check valve, that closes or is already closed when the waste tank 28 is detached from the housing 14. This prevents spent sterilization fluid from draining from the bottom of the waste tank 28. Referring back to FIGS. 11-13, the cartridge 26 may include a ring or handle 88 which the use may grasp to separate the cartridge 26 from the waste tank 28. The waste tank 28 then is emptied by, for example, pouring the fluid out of a top opening 90 in the tank 28, and the cartridge 26 is disposed of. A new cartridge 26 is nested with the waste tank 28, and the cartridge and waste tank are attached to the housing 14. The cartridge 28 may include an openable barrier initially covering the opening 35 which is in communication with flow path 32. In one embodiment, the openable barrier may be a breakable foil, which may be pierced by upright 33 extending from the housing 14 to initial fluid communication between the cartridge 28 and the flow path 32. The upright 33 may have an eyelet or opening 37 in communication with the flow path 32.

It should be understood that the kits described herein are merely exemplary and that the kits may include additional components, such as a magnet configured to secure the lid of the housing in its closed condition, without departing from the scope of the present disclosure.

FIGS. 14-23 illustrate another embodiment of a reusable urinary catheter kit 110. In the embodiment of FIGS. 14-17 and 21-23, the kit 110 includes a housing or body 114 having a base 116 with top and bottom ends 118 and 120. The outer shape of the kit is generally rectangular or trapezoidal in shape. The base 116 defines a disinfecting chamber 122 (FIGS. 15 and 17) that has an opening 124 defined by the top end 118 of the base 116.

The kit 110 also includes a supply of the sterilization fluid, such as the illustrated cartridge or tank 126, and a waste collection tank 128, which are both removably attachable to the housing 114 (FIGS. 16 and 21-23). One or both of the cartridge 126 and waste tank 128 may be disposable. The cartridge 126 and waste tank 128 also may have complementary shapes that allow the cartridge 126 and waste tank 128 to engage, nest, dovetail or otherwise fit together. For example, in the illustrated embodiment, the waste tank 128 may include a hollow 127 (FIGS. 16 and 22) wherein the cartridge 126 is sized and shaped to fit within the hollow 127. In the illustrated embodiment the hollow 127 and cartridge 126 both have generally rectangular shapes. This allows the cartridge 126 to nest with the waste tank 128. In other embodiments, the cartridge 126 and hollow 127 could be other various shapes. In one embodiment, there is a friction fit between the cartridge 126 and waste tank 128, such that the two are removably attached to each other. The shapes and positions of the cartridge 126 and the waste tank 128 could be switched and the waste tank 128 could nest within the cartridge 126. In yet another embodiment, the waste tank 128 and cartridge 126 may not be in any physical contact.

Figure 17:
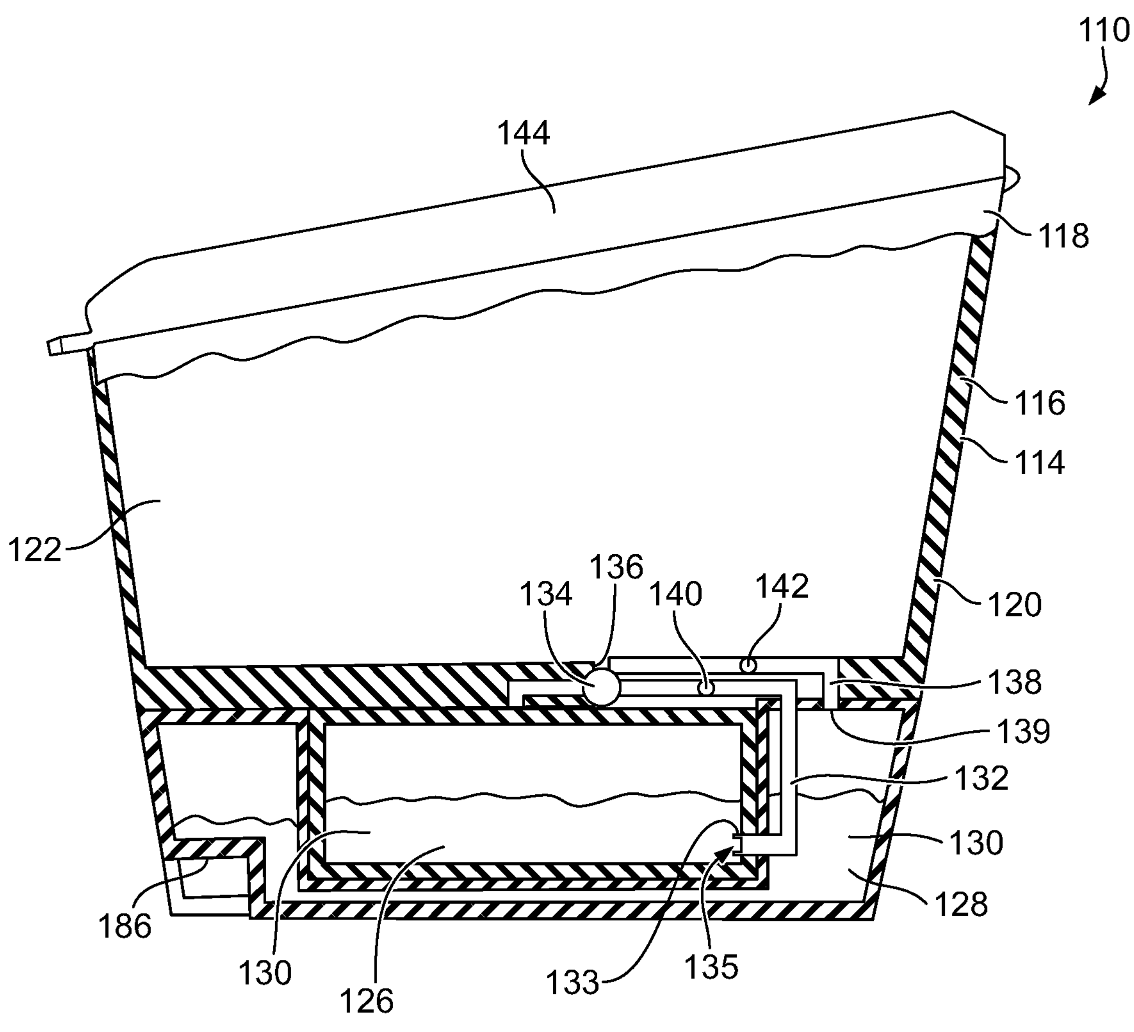
FIG. 17 is a partial cross-sectional view of the kit of FIG. 14.

When attached to the housing 114, the cartridge 126 and the waste tank 128 may be in selective fluid communication with the disinfecting chamber 122. Referring to FIG. 17, sterilization fluid 130 may flow from the cartridge 126 through a supply flow path 132 to a pump 134. Optionally, the supply flow path 132 may include an extension 133 that extends into opening 135 of the cartridge 126. The pump 134 may pump a select amount of sterilization fluid 130 through fill/drain flow path 136 into the disinfecting chamber 122. After disinfecting, the sterilization fluid 130 may flow through fill/drain flow path 136 back to pump 134, which may be a revisable pump. Pump 134 pumps the sterilization fluid 130 through waste flow path 138 and opening 139 in waste tank 128. Also, the supply flow path 132 and the waste flow path 138 may include valves 140 and 142 that are actuated during the filling and draining of the sterilization chamber 122. For example, when sterilization fluid 130 is being pumped from the cartridge 126 to the sterilization chamber 122, valve 140 may be open and valve 142 may be closed. When sterilization fluid 130 is being drained from the sterilization chamber 122, valve 142 may be open and valve 140 may be closed.

For embodiments in which a sterilization fluid is circulated through the kit, the fluid path may include one or more filters or screens configured to entrap debris circulating through the fluid path. Each filter or screen may be placed in any suitable location within the fluid path and may be variously configured without departing from the scope of the present disclosure. In an exemplary embodiment, the filter or screen may be provided as a flat mesh with pores that are sized and configured to entrap particulates that may be present in urine. In other embodiments, the filter or screen may be differently configured (e.g., being formed of a woven or non-woven material), including having any pore size and/or porosity. If multiple filters or screens are provided, they may be substantially identical or differently configured and may be positioned at any suitable location with respect to each other. In one embodiment, the filter or screen may be placed in the return loop returning fluid to the pump for recycling. In this embodiment, the filter entraps debris prior to the fluid entering the pump and being returned back into the compartment with the catheter.

A lid 144 is associated with the top end 118 of the base 116. The lid 144 is movable between a closed condition, in which the lid covers the opening 124 of the disinfecting chamber 122 (as in FIG. 14) and an open condition in which the lid 144 does not cover opening 124 (as in FIG. 15). In the illustrated embodiment, the lid 144 is pivotally secured to the top end 118 of the base 116. The lid 144 is movable between the closed condition, in which the lid 144 is pivoted toward the base 116 (as in FIG. 14) and an open condition in which the lid 144 is pivoted away from the base 116 (as in FIG. 15). More particularly, in the closed condition, the lid 144 is positioned to contact and overlay the base 116, covering the disinfecting chamber opening 124. The base 116 and lid 144 may be formed of a generally rigid material, such as a plastic material. The lid may also include the user interface 146, which the user interacts with to commence sterilization and which provides the user with an indication of stages of the sterilization process.

Referring to FIGS. 15 and 18-20, chassis 148 is removably positioned within the disinfecting chamber 122 (FIGS. 5 and 9). The chassis 148 may have a shape that is generally similar to that of the chamber 122. For example, chassis 148 may be generally rectangular. The chassis 148 also may be formed of a generally rigid material, such as a plastic material, with a reusable urinary catheter 112 removably secured to the chassis 148, such as by being at least partially wrapped around the chassis 148. The chassis 148 includes a body 150 having a frame 152 for holding the catheter 112 and a hook 154 extending from the frame 152 for handling and hanging the chassis 148.

The chassis 148 may be variously configured without departing from the scope of the present disclosure. In the illustrated embodiment, the frame 152 of the chassis 148 includes opposed catheter clips 156 and 158, with catheter tube 160 of the reusable urinary catheter 112 removably received by clips 156 and 158. The illustrated chassis 148 further includes at least one wall 160 between the clips 156 and 158. The wall 160 may be arcuate and it has a groove 162 that receives the catheter tube 164 to maintain the tube in a bent configuration.

Figures 18, 19, 20:
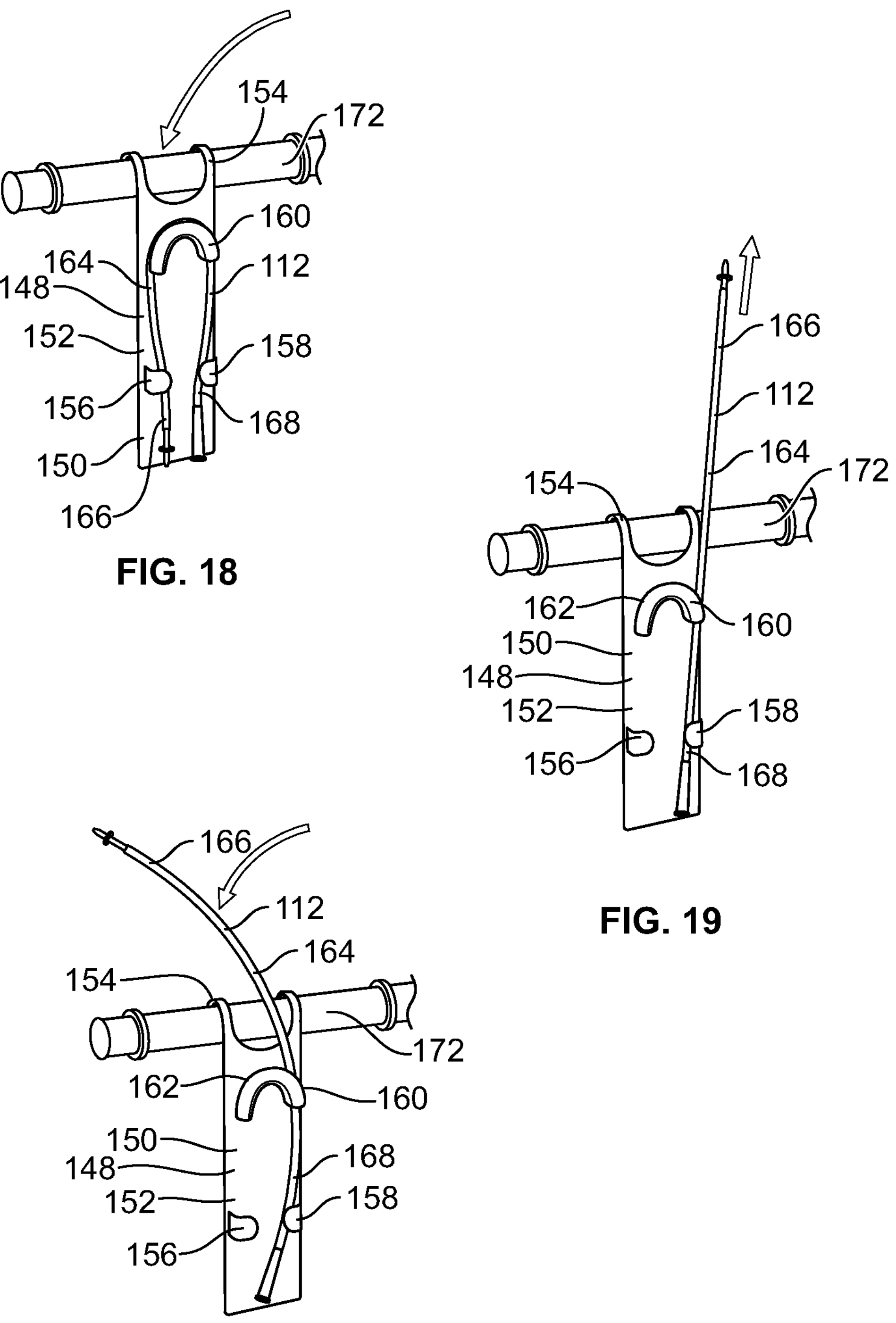
FIGS. 18-20 are perspective views of a chassis and reusable urinary catheter of the kit of FIG. 14.
Figures 21, 22, 23:
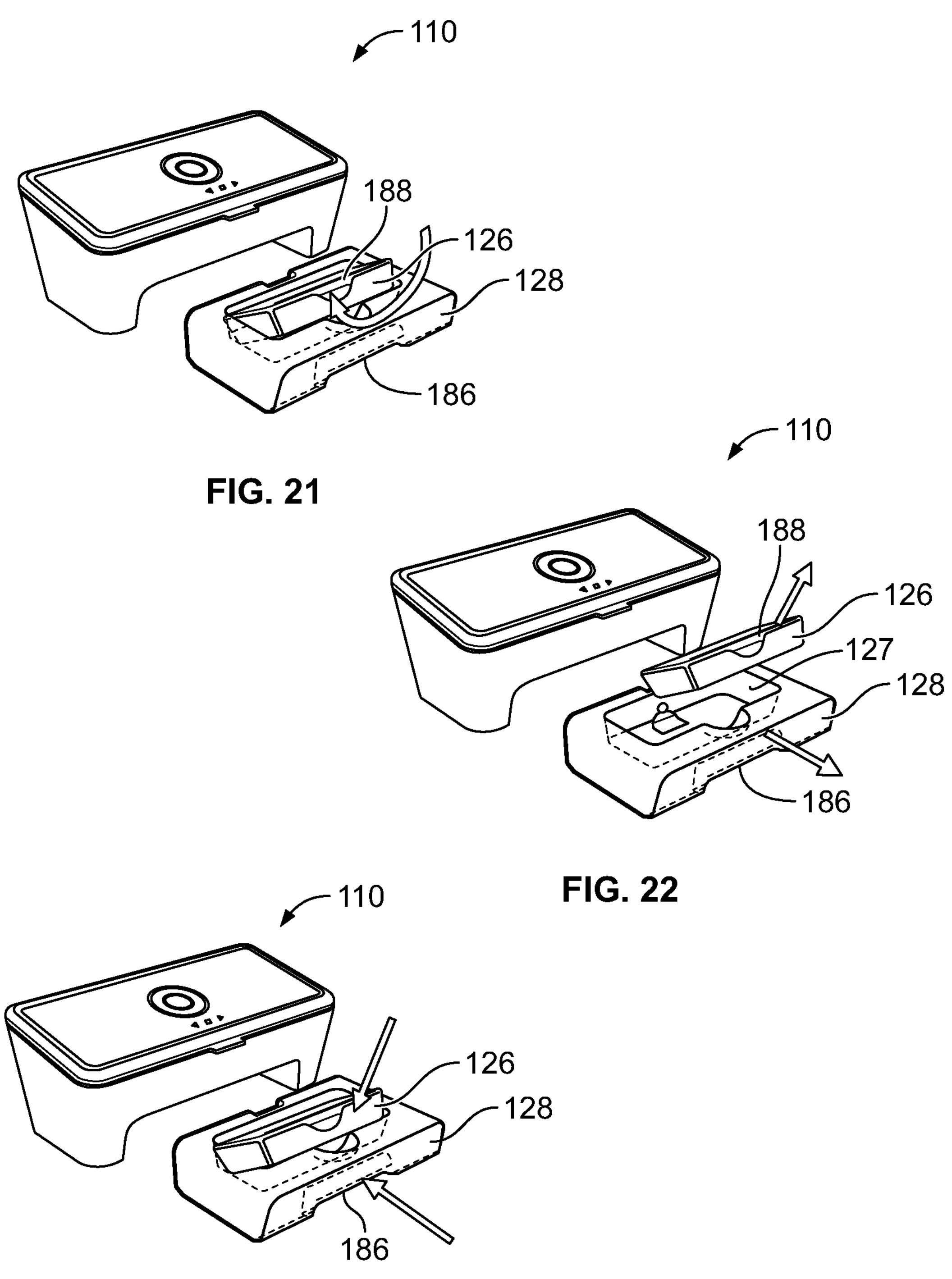
FIGS. 21-23 are perspective views of the reusable urinary catheter kit of FIG. 14, showing the removal and replacement of the sterilization fluid supply and the waste collection tank.

To secure the reusable urinary catheter 112 to the illustrated chassis 148, one of the proximal end 166 and the distal end 168 of the catheter tube 164 is pressed into one of the clips 156 and 158, followed by wrapping the catheter tube 164 around wall 160 of the frame, with a middle portion of the catheter tube received by the groove 162 of the wall (FIGS. 18 and 20). The other end of the proximal and distal ends 166 and 168 of the catheter tube 164 is pressed into the other one of the clips 156 and 158 (FIG. 20). The installation process may be reversed to dissociate the reusable urinary catheter 112 from the chassis 148 (FIG. 19).

In use, the lid 144 of the housing 114 is opened and the user removes the chassis 148 from the disinfecting chamber 122. Next, the chassis 148 is removed from the base 116 (FIG. 15) and the reusable urinary catheter 112 is all or partially dissociated from the chassis 148 (FIG. 19), as described above. During dissociation of the catheter 112 from the chassis 148, the user may use the hook 152 to hang the chassis 148 on for example a towel bar 172 (FIGS. 18-20). The user then uses the reusable urinary catheter 112 for catheterization. Following catheterization, the reusable urinary catheter 112 is reconnected to the chassis 148 (FIG. 20) and then the chassis 148 is returned to the disinfecting chamber 122. The lid 144 is then moved from its open condition to its closed condition, as in FIG. 14. The user then initiates the sterilization process in which the sterilization fluid flows from the cartridge 126 into the disinfecting chamber 122. The sterilization fluid remains within the disinfecting chamber 122 for a period time sufficient to sterilize the catheter. Optionally, an agitator or fluid circulator may be included in the disinfecting chamber 122 to move the sterilization fluid within the chamber. If the sterilization fluid comprises a foam, the agitator or fluid circulator may foam the sterilization fluid and/or the sterilization fluid may be foamed by the pump or a restriction in the supply line.

The sterilization fluid then is drained from the disinfecting chamber 122 and flows into the waste tank 128. After the sterilization fluid has been drained from the chamber 122 to the waste tank, the sterilization process is completed and the catheter 112 is ready to be reused for catheterization.

Optionally, at least one light source is associated with the base 116 and/or the lid 144 and is configured to irradiate at least a portion of the reusable urinary catheter 112 with light to refresh the hydrophilic coating, if one is present.

For any of the embodiments described herein that include a sterilizing light source and a hydrophilic coated catheter, the light source may be used to refresh or replenish the hydrophilic coating of the catheter. Hydrophilic catheter coatings are formed from a hydrophilic polymer. In one embodiment the sterilization fluid or hydration medium may contain a hydrophilic polymer in the fluid/medium wherein the hydrophilic polymer is the same polymer as that in the coating or one that is compatible with the hydrophilic polymer of the coating. When the sterilization fluid or hydration medium comes into contact with the hydrophilic coating of the catheter, some of the hydrophilic polymer from the fluid/medium remains on or becomes entangled with the polymer of the hydrophilic coating. Exposure to the sterilizing light source promotes or initiates cross-linking between the hydrophilic polymer of the fluid/medium and the hydrophilic coating of the catheter, thereby refreshing or replenishing the hydrophilic coating with new or additional polymer material.

Referring to FIGS. 17 and 21-23, after the cartridge 126 is spent or otherwise needs to be changed, the cartridge 126 and waste tank 128 may be detached from the housing 114. In the illustrated embodiment, the waste tank 128 includes a handle 186, which is grasped and pulled by the user to detach the waste tank 128 and cartridge 126 from the housing 114. The cartridge 126 may include a handle 188 which the use may grasp to separate the cartridge 126 from the waste tank 128. The waste tank 128 then is emptied by, for example, pouring the fluid out of the opening 139 (FIG. 17) of the tank 128, and the cartridge 126 is disposed of. A new cartridge 126 is nested with the waste tank 128, and the cartridge and waste tank are attached to the housing 114. The cartridge 128 may include an openable barrier initially covering the opening 135 which is in communication with flow path 132. In one embodiment, the openable barrier may be a breakable foil, which may be pierced by extension 133 to initial fluid communication between the cartridge 128 and the flow path 132.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A reusable urinary catheter kit, comprising:

a housing including:

a base defining a disinfecting chamber, the base having a bottom end and a top end, the top end of the base defining an opening of the disinfecting chamber;

a lid associated with the top end of the base, movable between a closed condition and an open condition, in the closed condition the lid overlaying the base and covering the opening of the disinfecting chamber and in the open condition the lid being moved away from the base to uncover the opening of the disinfecting chamber;

a chassis removably positioned within the housing;

a reusable urinary catheter removably secured to the chassis;

a lifting member within the housing wherein the lifting member lifts the chassis when the lid is moved to the open condition;

a removable supply of sterilization fluid in fluid communication with the disinfecting chamber; and a waste tank in communication with the disinfecting chamber.

2. The reusable urinary catheter kit of claim 1, wherein the lid is pivotally secured to the top end of the base and is pivoted away from the base when in the open condition.

3. The reusable urinary catheter kit of claim 1, wherein the lifting member is connected to the lid.

4. The reusable urinary catheter kit of claim 3, wherein the lifting member comprises an arm connected to the lid.

5. The reusable urinary catheter kit of claim 1, further including one or more pumps for pumping sterilization fluid from the supply of sterilization fluid into the disinfecting chamber and pumping sterilization fluid from the disinfecting chamber to the waste tank.

6. The reusable urinary catheter kit of claim 1, wherein the waste tank is removably secured to the housing.

7. The reusable urinary catheter kit of claim 1, wherein the supply of sterilization fluid comprises a cartridge of sterilization fluid.

8. A reusable urinary catheter kit, comprising:

a housing including:

a base defining a disinfecting chamber, the base having a bottom end and a top end, the top end of the base defining an opening of the disinfecting chamber;

a lid associated with the top end of the base, movable between a closed condition and an open condition, in the closed condition the lid overlaying the base and covering the opening of the disinfecting chamber and in the open condition the lid being moved away from the base to uncover the opening of the disinfecting chamber;

a chassis removably positioned within the housing;

a reusable urinary catheter removably secured to the chassis, wherein the reusable urinary catheter is removably secured to the chassis by being at least partially wrapped around the chassis;

a removable supply of sterilization fluid in fluid communication with the disinfecting chamber; and a waste tank in communication with the disinfecting chamber.

9. A reusable urinary catheter kit, comprising:

a housing including:

a base defining a disinfecting chamber, the base having a bottom end and a top end, the top end of the base defining an opening of the disinfecting chamber;

a lid associated with the top end of the base, movable between a closed condition and an open condition, in the closed condition the lid overlaying the base and covering the opening of the disinfecting chamber and in the open condition the lid being moved away from the base to uncover the opening of the disinfecting chamber;

a chassis removably positioned within the housing;

a reusable urinary catheter removably secured to the chassis, wherein the chassis comprises one or more clips, and the reusable urinary catheter is received in the one or more clips;

a removable supply of sterilization fluid in fluid communication with the disinfecting chamber; and a waste tank in communication with the disinfecting chamber.

10. A reusable urinary catheter kit, comprising:

a housing including:

a base defining a disinfecting chamber, the base having a bottom end and a top end, the top end of the base defining an opening of the disinfecting chamber;

a lid associated with the top end of the base, movable between a closed condition and an open condition, in the closed condition the lid overlaying the base and covering the opening of the disinfecting chamber and in the open condition the lid being moved away from the base to uncover the opening of the disinfecting chamber;

a chassis removably positioned within the housing;

a reusable urinary catheter removably secured to the chassis, wherein the chassis comprises a wall having a groove, and the reusable urinary catheter is received into the groove of the wall;

a removable supply of sterilization fluid in fluid communication with the disinfecting chamber; and a waste tank in communication with the disinfecting chamber.

11. The reusable urinary catheter kit of claim 1, wherein the chassis has a shape similar to that of a shape of the disinfecting chamber.

12. The reusable urinary catheter kit of claim 1, wherein the chassis comprises opposed first and second clips and a wall having an arcuate groove; and the reusable urinary catheter comprises a catheter tube removably received in the first and second clips and the groove of the wall.

13. The reusable urinary catheter kit of claim 1, further comprising at least one light source associated with the base and/or the lid and configured to irradiate at least a portion of the reusable urinary catheter.

14. The reusable urinary catheter kit of claim 1, wherein the supply of sterilization fluid is disposable.

15. The reusable urinary catheter kit of claim 8, further including one or more pumps for pumping sterilization fluid from the supply of sterilization fluid into the disinfecting chamber and pumping sterilization fluid from the disinfecting chamber to the waste tank.

16. The reusable urinary catheter kit of claim 8, wherein the waste tank is removably secured to the housing.

17. The reusable urinary catheter kit of claim 8, wherein the supply of sterilization fluid comprises a cartridge of sterilization fluid.

18. The reusable urinary catheter kit of claim 8, further comprising at least one light source associated with the base and/or the lid and configured to irradiate at least a portion of the reusable urinary catheter.

19. The reusable urinary catheter kit of claim 8, wherein the supply of sterilization fluid is disposable.

20. The reusable urinary catheter kit of claim 9, further including one or more pumps for pumping sterilization fluid from the supply of sterilization fluid into the disinfecting chamber and pumping sterilization fluid from the disinfecting chamber to the waste tank.

21. The reusable urinary catheter kit of claim 9, wherein the waste tank is removably secured to the housing.

22. The reusable urinary catheter kit of claim 9, wherein the supply of sterilization fluid comprises a cartridge of sterilization fluid.

23. The reusable urinary catheter kit of claim 9, further comprising at least one light source associated with the base and/or the lid and configured to irradiate at least a portion of the reusable urinary catheter.

24. The reusable urinary catheter kit of claim 10, wherein the supply of sterilization fluid is disposable.

25. The reusable urinary catheter kit of claim 10, further including one or more pumps for pumping sterilization fluid from the supply of sterilization fluid into the disinfecting chamber and pumping sterilization fluid from the disinfecting chamber to the waste tank.

26. The reusable urinary catheter kit of claim 10, wherein the waste tank is removably secured to the housing.

27. The reusable urinary catheter kit of claim 10, wherein the supply of sterilization fluid comprises a cartridge of sterilization fluid.

28. The reusable urinary catheter kit of claim 10, further comprising at least one light source associated with the base and/or the lid and configured to irradiate at least a portion of the reusable urinary catheter.

29. The reusable urinary catheter kit of claim 10, wherein the supply of sterilization fluid is disposable.

* * * * *